(12) United States Patent
Ressel et al.

(10) Patent No.: US 10,494,350 B2
(45) Date of Patent: Dec. 3, 2019

(54) PROCESS FOR PRODUCING BIGUANIDINE SALTS AND S-TRIAZINES

(71) Applicant: Bayer CropScience Aktiengesellschaft, Monheim am Rhein (DE)

(72) Inventors: Hans-Joachim Ressel, Hattersheim (DE); Mark James Ford, Wiesbaden-Breckenheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/758,958

(22) PCT Filed: Sep. 5, 2016

(86) PCT No.: PCT/EP2016/070858
§ 371 (c)(1),
(2) Date: Mar. 9, 2018

(87) PCT Pub. No.: WO2017/042126
PCT Pub. Date: Mar. 16, 2017

(65) Prior Publication Data
US 2019/0040019 A1   Feb. 7, 2019

(30) Foreign Application Priority Data
Sep. 11, 2015 (EP) ...................... 15184873

(51) Int. Cl.
*C07C 277/08* (2006.01)
*C07D 251/48* (2006.01)
*C07C 279/26* (2006.01)

(52) U.S. Cl.
CPC .......... *C07D 251/48* (2013.01); *C07C 277/08* (2013.01); *C07C 279/26* (2013.01)

(58) Field of Classification Search
None
See application file for complete search history.

(56) References Cited

U.S. PATENT DOCUMENTS 8,759,584 B2    6/2014  Ford
2017/0073331 A1*  3/2017  Kim ...................... C07C 279/04

FOREIGN PATENT DOCUMENTS

WO    2008026757 A1    3/2008
WO    2009077059 A1    6/2009

OTHER PUBLICATIONS

PCT International Search Report for PCT/EP2016/070858, dated Nov. 18, 2016.

* cited by examiner

*Primary Examiner* — Sudhakar Katakam
*Assistant Examiner* — Jennifer C Sawyer
(74) *Attorney, Agent, or Firm* — McBee Moore Woodward & Vanik IP, LLC

(57) ABSTRACT

A process for producing biguanidine salts of formula (III) and s-triazines of formula (V) is described.

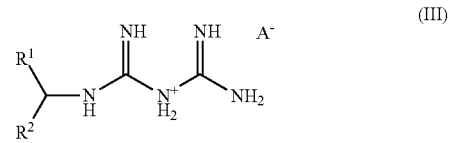

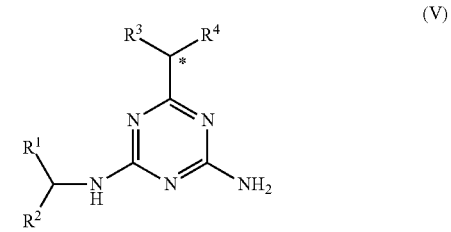

Therein, $R^1$ and $R^2$ are in each case hydrogen, halogen and alkyl, and $R^3$ and $R^4$ are in each case hydrogen, alkyl, cycloalkyl and aryl.

14 Claims, No Drawings

PROCESS FOR PRODUCING BIGUANIDINE SALTS AND S-TRIAZINES

CROSS-REFERENCE TO RELATED APPLICATIONS

This application is a National Stage entry of International Application No. PCT/EP2016/070858, filed Sep. 5, 2016, which claims priority to European Patent Application No. 15184873.6, filed Sep. 11, 2015.

BACKGROUND

Field

The invention relates to a process for producing biguanidine salts and s-triazines.

Symmetrical triazines, known as 1,3,5-triazines or s-triazines, are important intermediates or even constituents of many active pharmaceutical and agrochemical ingredients depending on the type of substituents. The production thereof often proceeds via biguanidines which are then reacted with a carboxylic acid derivative for example, to afford the desired s-triazines. These reactions often proceed only with low yields and large excesses of the usually costly carboxylic acid derivatives are therefore employed to enhance the yield. A further disadvantage of the known methods is that in the reaction of a biguanidine with a chiral carboxylic acid derivative, such as lactic esters or α-halogenocarboxylic esters, the reaction proceeds with a great loss of stereochemical information at the alpha-carbon atom of the carboxylic acid derivative.

Description of Related Art

Known methods for producing biguanidine salts are the reaction of cyanamide with guanidines and the reaction of cyanoguanidine with ammonium salts at high temperatures in solution or in the melt. However, these methods have the disadvantages that they result in inadequate yields and inadequate purities or else in mixtures from which the desired biguanidine salt is difficult to isolate. For instance the biguanidine salt formed can undergo thermal degradation to form guanidine derivatives which hamper further use. These methods must also be regarded as disadvantageous from a safety aspect. For instance, decomposition reactions often proceed in highly exothermic fashion even at low onset temperature. A further safety issue is the accumulation of cyanoguanidine over the course of the reaction with ammonium salts.

To overcome these disadvantages, WO 2009/077059 A1 proposes reacting amines, or hydrochlorides thereof, with cyanoguanidine with aluminum alkoxides to afford intermediate biguanidino-aluminum complexes which then further react with carboxylic acid derivatives to afford s-triazines. While the reaction does proceed with very good yields, the required large excesses of cyanoguanidine and of aluminum alkoxides result in considerable amounts of waste which require costly and complex disposal.

SUMMARY

The present invention has for its object the provision of a process for producing biguanidine salts and s-triazines which overcomes the disadvantages of the processes known from the prior art.

A process for producing biguanidine salts and s-triazines has now been found which
can be carried out with a great many amines of different structures,
requires only a small excess of cyanoguanidine,
proceeds without accumulation of cyanoguanidine,
results in only small amounts of byproducts,
results in high yields, and
proceeds without loss of stereochemical information.

The use of certain solvents is an essential feature of the process according to the invention because the biguanidine salt to be produced is added in catalytic amounts at the start of the reaction. It is been found that the biguanidine salt reacts autocatalytically and the abovementioned advantages are realized in particular when catalytic amounts of the biguanidine salt to be produced are added at the start of the reaction. Such catalytic amounts may be obtained by preliminary experiments, optionally also by other processes (all achieving lower yields), and then employed in the process according to the invention. The thus produced biguanidine salt may be
A) isolated and stored as an intermediate or
B) directly reacted with a suitable reagent to afford a 1,3,5-triazine.

DETAILED DESCRIPTION OF A PREFERRED EMBODIMENT

One aspect of the present invention is accordingly A) a process for producing biguanidine salts of formula (III), wherein
a) an amine of formula (I) is converted into a salt (II) with an acid $H^+A^-$,
b) cyanoguanidine and 0.5 to 10 mol percent of the biguanidine salt (III) to be produced, based on the amine of formula (I), in a polar aprotic solvent are metered in with stirring at elevated temperature,
c) after cooling the thus obtained reaction mixture is suctioned off, washed with solvent and dried, and
d) where the substituents are as defined hereinbelow:

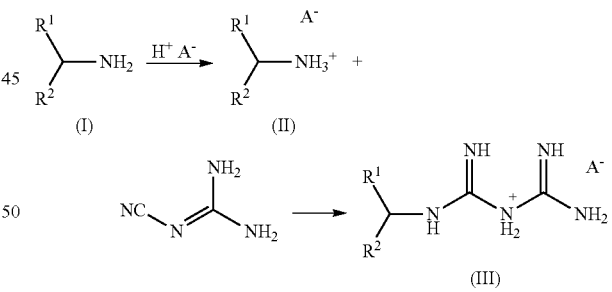

$R^1$ is hydrogen, $(C_1-C_8)$-alkyl, $(C_3-C_8)$-cycloalkyl, phenyl, naphthyl, $(C_1-C_4)$-alkylphenyl, wherein the four last-mentioned radicals are substituted by n radicals from the group consisting of methyl, ethyl, propyl and methoxy, $R^2$ is $(C_1-C_8)$-alkyl, $(C_3-C_8)$-cycloalkyl, phenyl, naphthyl, phenyl-$(C_1-C_4)$-alkyl, wherein these four abovementioned radicals are substituted by n radicals from the group consisting of methyl, ethyl, propyl, methoxy and $(C_3-C_4)$-cycloalkyl,
or
$R^1$ and $R^2$ together with the carbon atom to which they are bonded form a radical from the group consisting of $(C_3-C_8)$-cycloalkyl, phenyl-$(C_3-C_8)$-cycloalkyl,

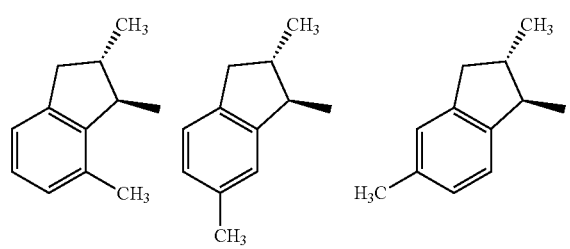

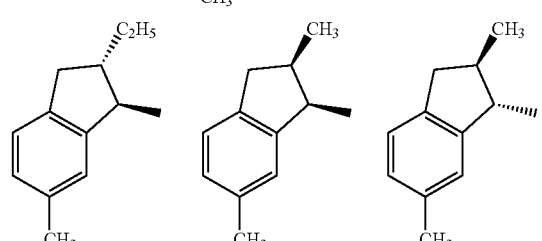

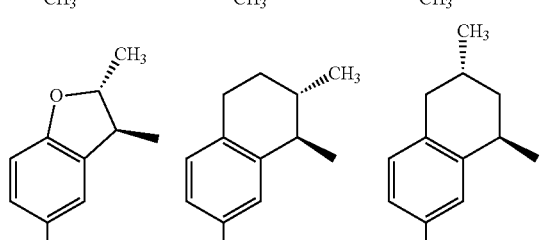

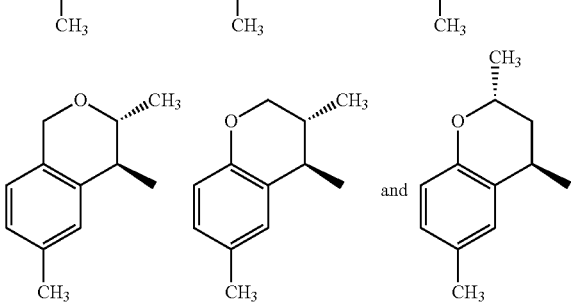

A⁻ is an anion of an acid, n is 0, 1, 2 or 3.

A further aspect of the present invention is B) a process for producing s-triazines of formula (V), wherein a) an amine of formula (I) is converted into a salt (II) with an acid H⁺A⁻, b) cyanoguanidine and 0.5 to 10 mol percent of the biguanidine salt (III) to be produced, based on the amine of formula (I), in a polar aprotic solvent are metered in with stirring at elevated temperature, c) after complete reaction a phase transfer catalyst and a base are added, d) a carboxylic acid derivative of formula (IV) is metered in, and e) where the substituents are as defined hereinbelow:

$$\underset{R^2}{\overset{R^1}{\diagdown}}CH-NH_2 \xrightarrow{H^+A^-} \underset{R^2}{\overset{R^1}{\diagdown}}CH-NH_3^+ \quad \overset{A^-}{\phantom{+}} +$$

(I) (II)

$$NC-N=\overset{NH_2}{\underset{NH_2}{C}} \longrightarrow \underset{R^2}{\overset{R^1}{\diagdown}}CH-\underset{H}{\overset{NH}{N}}-\overset{+}{\underset{H_2}{N}}-\overset{NH}{\underset{NH_2}{C}} \quad A^-$$

(III)

$$\underset{R^2}{\overset{R^1}{\diagdown}}CH-\underset{H}{\overset{NH}{N}}-\overset{+}{\underset{H_2}{N}}-\overset{NH}{\underset{NH_2}{C}}\;A^- + \underset{X}{\overset{R^3\;\;R^4}{\diagdown*\diagup}} \xrightarrow{\text{PTK, Base}}$$

(III) (IV)

(V)

R¹ is hydrogen, (C₁-C₈)-alkyl, (C₃-C₈)-cycloalkyl, phenyl, naphthyl, (C₁-C₄)-alkylphenyl, wherein the four last-mentioned radicals are substituted by n radicals from the group consisting of methyl, ethyl, propyl and methoxy, R² is (C₁-C₈)-alkyl, (C₃-C₈)-cycloalkyl, phenyl, naphthyl, phenyl-(C₁-C₄)-alkyl, wherein these four abovementioned radicals are substituted by n radicals from the group consisting of methyl, ethyl, propyl, methoxy and (C₃-C₄)-cycloalkyl, or R¹ and R² together with the carbon atom to which they are bonded form a radical from the group consisting of (C₃-C₈)-cycloalkyl, phenyl-(C₃-C₈)-cycloalkyl,

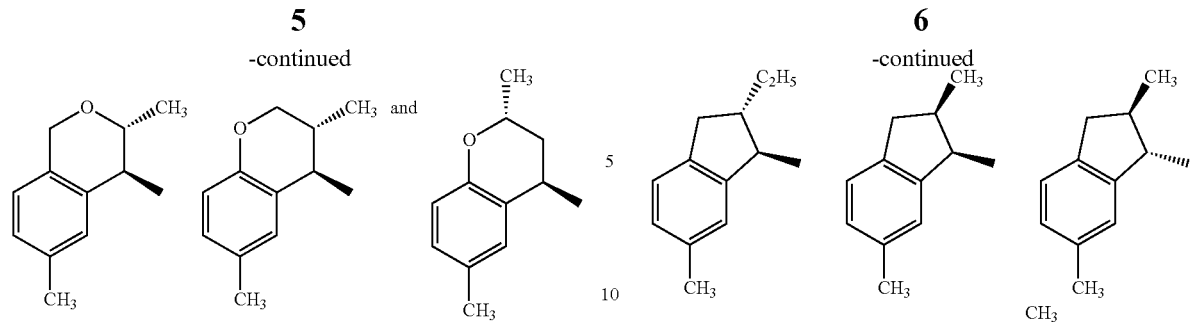

A⁻ is an anion of an acid, n is 0, 1, 2 or 3,

R³ is hydrogen, halogen, $(C_1-C_6)$-alkyl, $(C_1-C_6)$-alkoxy, $(C_3-C_8)$-cycloalkyl, phenyl, wherein the three last-mentioned radicals are substituted by n radicals from the group consisting of methyl, ethyl, propyl and methoxy, R⁴ is hydrogen, halogen, $(C_1-C_6)$-alkyl, $(C_1-C_6)$-alkoxy, $(C_3-C_8)$-cycloalkyl, phenyl, wherein the three last-mentioned radicals are substituted by n radicals from the group consisting of methyl, ethyl, propyl and methoxy, X is $(C_1-C_6)$-alkoxycarbonyl, cyano or chlorocarbonyl.

The carbon atom marked with an asterisk (*) is a chiral center provided that R³ and R⁴ are different and neither of these radicals is hydrogen.

In the formulae (I), (II), (III), (IV), (V) and subsequent formulae, alkyl radicals having more than two carbon atoms may be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl.

Halogen is fluorine, chlorine, bromine or iodine, preferably fluorine or chlorine.

If a group is polysubstituted by radicals, this is to be understood as meaning that this group is substituted by one or more identical or different radicals selected from the radicals mentioned.

The anion A⁻ is, for example, Cl⁻, Br⁻, I⁻, $HSO_4^-$, $HCO_3^-$ or $H_3CSO_3^-$.

In a preferred embodiment of invention aspect A), the substituents are defined as follows:

R¹ is hydrogen, $(C_1-C_8)$-alkyl, $(C_3-C_8)$-cycloalkyl, phenyl, $(C_1-C_4)$-alkylphenyl, wherein the three last-mentioned radicals are substituted by n radicals from the group consisting of methyl, ethyl, propyl and methoxy, R² is $(C_1-C_8)$-alkyl, $(C_3-C_8)$-cycloalkyl, phenyl, naphthyl or phenyl-$(C_1-C_4)$-alkyl, or R¹ and R² together with the carbon atom to which they are bonded form a radical from the group consisting of $(C_3-C_8)$-cycloalkyl, phenyl-$(C_3-C_8)$-cycloalkyl,

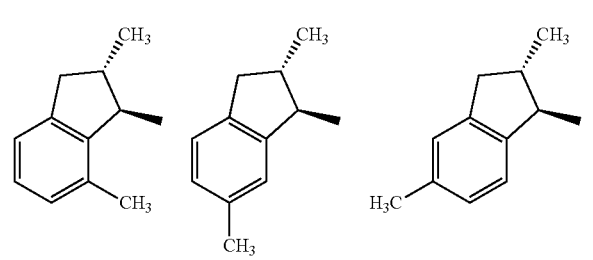

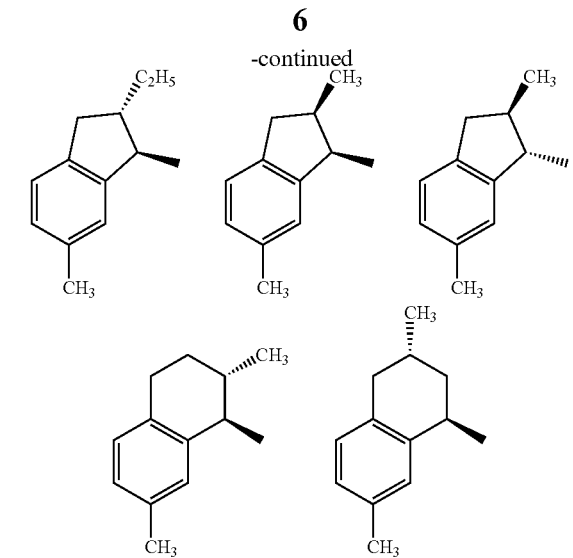

A⁻ is Cl⁻, Br⁻ or $HSO_4^-$, n is 0, 1, 2 or 3.

In a preferred embodiment of invention aspect B), the substituents are defined as follows:

R¹ is hydrogen, $(C_1-C_8)$-alkyl, $(C_3-C_8)$-cycloalkyl, phenyl, $(C_1-C_4)$-alkylphenyl, wherein the three last-mentioned radicals are substituted by n radicals from the group consisting of methyl, ethyl, propyl and methoxy, R² is $(C_1-C_8)$-alkyl, $(C_3-C_8)$-cycloalkyl, phenyl, phenyl-$(C_1-C_4)$-alkyl, or R¹ and R² together with the carbon atom to which they are bonded form a radical from the group consisting of $(C_3-C_8)$-cycloalkyl, phenyl-$(C_3-C_8)$-cycloalkyl,

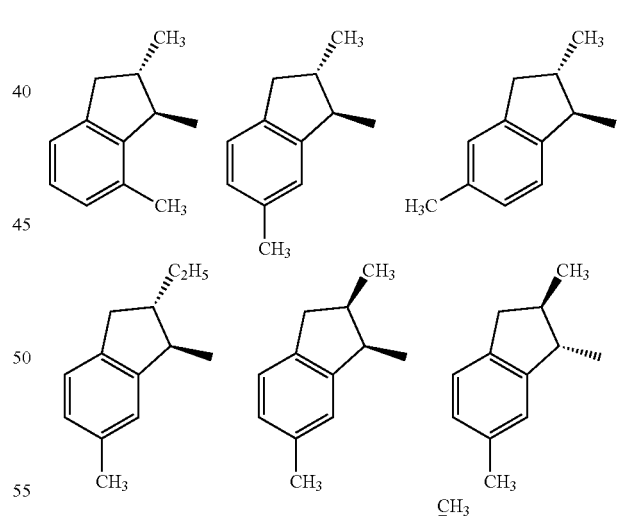

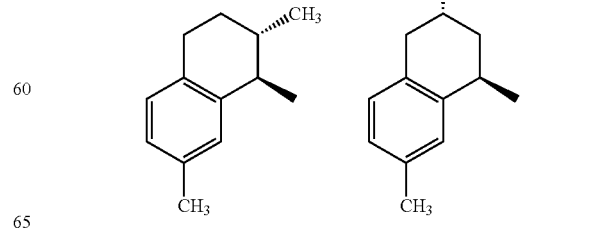

A⁻ is Cl⁻, Br⁻ or $HSO_4^-$, n is 0, 1, 2 or 3,
$R^3$ is hydrogen, chlorine, fluorine, $(C_1$-$C_6)$-alkyl or $(C_1$-$C_6)$-alkoxy,
$R^4$ is hydrogen, chlorine, fluorine, $(C_1$-$C_6)$-alkyl or $(C_1$-$C_6)$-alkoxy,
X is $(C_1$-$C_6)$-alkoxycarbonyl.

In a particularly preferred embodiment of invention aspect A),
the substituents are defined as follows:
$R^1$ and $R^2$ together with the carbon atom to which they are bonded form the radical

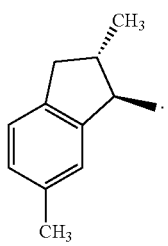

$A^-$ is $Cl^-$.

In a particularly preferred embodiment of invention aspect B),
the substituents are defined as follows:
$R^1$ and $R^2$ together with the carbon atom to which they are bonded form the radical

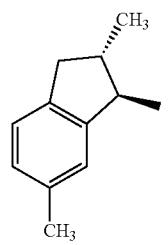

$A^-$ is $Cl^-$,
$R^3$ is fluorine,
$R^4$ is methyl,
X is $(C_1$-$C_6)$-alkoxycarbonyl.

The amine salts (II) can be produced by reaction of the free amines of formula (I) with an acid, such as hydrogen chloride, hydrogen bromide, hydrogen iodide, sulfuric acid, nitric acid, carbonic acid, sulfonic acids such as methanesulfonic acid, by methods known to those skilled in the art. The free amines are commercially available or can be produced by methods known to those skilled in the art.

The reaction in step b) of both abovementioned invention aspects A) and B) is typically carried out at a temperature from 100° C. to the boiling point of the solvent, preferably 140° C. to 148° C., and with an excess of 5% to 10% of cyanoguanidine based on the amine salt of formula (II). Suitable solvents include anisole, n-hexyl acetate, dichlorobenzenes and mixtures thereof. Anisole is preferred. This reaction may be carried out at atmospheric pressure and at elevated pressure.

The reaction in step B) of both abovementioned invention aspects A) and B) is preferably carried out with 0.5 to 2 mol percent of the biguanidine salt (III) to be produced.

The phase transfer catalyst employed in step c) of the second-named invention aspect B) may be selected from a great many phase transfer catalysts known to those skilled in the art. Suitable phase transfer catalysts are polyethylene glycols, quaternary ammonium salts and crown ethers. Preference is given to polyethylene glycols such as PEG 2000.

The phase transfer catalyst in step c) of the second-named invention aspect B) is typically added in an amount from 0 to 10, preferably 0.5 to 5, particularly preferably 0.5 to 3, very particularly preferably 0.5 to 1.5, mol percent based on the amine of formula (I).

The base in step c) of the second-named invention aspect B) is typically added in an amount from 100 to 500, preferably 100-400, particularly preferably 200 to 400, mol percent based on the amine of formula (I).

The carboxylic acid derivative of formula (IV) in step c) of the second-named invention aspect B) is advantageously added in an amount from 100 to 250, preferably 100-150, particularly preferably 100-40, mol percent based on the amine of formula (I).

Suitable bases in step c) and d) of the second-named invention aspect B) are carbonates of alkali metals and alkaline earth metals. Potassium carbonate, sodium carbonate, lithium carbonate, calcium carbonate and magnesium carbonate are particularly suitable. Potassium carbonate and sodium carbonate are preferred, potassium carbonate being particularly preferred.

The individual steps of the process according to the invention are advantageously carried out under a protective gas atmosphere.

The exemplary embodiments which follow more particularly elucidate the invention.

EXAMPLE 1 (AS PER INVENTION ASPECT A)

Production of amino-N{N-[(1R,2S)-2,6-dimethyl-2,3-dihydro-1H-inden-1-yl]carbamimidoyl}iminomethanaminium chloride 13.03 g (0.080 mol) of (1R,2S)-2,6-dimethyl-2,3-dihydro-1H-inden-1-yl-amine were initially charged in 110 ml of methoxybenzene under an argon atmosphere and cooled to 0° C. 8.26 g (0.082 mol) of conc. (36%) HCl were then added dropwise with stirring. The mixture was allowed to reach room temperature and stirred for a further 30 minutes. The mixture was then heated under vacuum (20 mbar) to 100-120° C. in a bath and a mixture of water and methoxybenzene was distilled off until water stopped passing over. Still under an argon atmosphere, 1.22 g (4.5 mmol) of the amino-N{N-[(1R,2S)-2,6-dimethyl-2,3-dihydro-1H-inden-1-yl]carbamimidoyl}iminomethanaminium chloride to be produced (obtained from a preliminary experiment) were added followed by addition of 7.5 g (88 mmol) of cyanoguanidine via a metered solids addition over 2.5 hours at 145-149° C. The progress of the reaction was monitored by means of HPLC. The mixture was then stirred for a further 1.5 hours at 145-148° C. and then allowed to cool to 75° C. 8 ml of methanol were then added and the mixture was cooled further to 20° C. The crystalline product was suctioned off under vacuum via a frit and washed twice with 10 ml of ethyl acetate in each case. Drying under vacuum (70° C./15 mbar) afforded 22.25 g of amino-N{N-[(1R,2S)-2,6-dimethyl-2,3-dihydro-1H-inden-1-yl]carbamimidoyl}iminomethanaminium chloride in 99% purity. Taking into account the catalytically employed amount this corresponds to a yield of 92.4% of theory.

EXAMPLE 2 (AS PER INVENTION ASPECT A)

Under conditions analogous to those mentioned in example 1, 1-cyclobutyl-3-phenylpropylamine afforded the corresponding biguanidine chloride in 78% yield.

EXAMPLE 3 (AS PER INVENTION ASPECT A)

Under conditions analogous to those mentioned in example 1, (1R,2S)-2,6-dimethyl-2,3-dihydro-1H-inden-1-yl-amine and carbonic acid afforded the corresponding biguanidine carbonate in 90% yield.

EXAMPLE 4 (AS PER INVENTION ASPECT A)

Under conditions analogous to those mentioned in example 1, (1R,2S)-2,6-dimethyl-2,3-dihydro-1H-inden-1-yl-amine and hydrogen bromide afforded the corresponding biguanidine bromide in 69% yield.

EXAMPLE 5 (AS PER INVENTION ASPECT B)

Production of N-[(1R,2S)-2,6-dimethyl-2,3-dihydro-1H-inden-1yl]-6-[(1R)-1-fluoroethyl]-1,3,5-triazine-2,4-diamine 12.0 g (73.6 mmol) of (1R,2S)-2,6-dimethyl-2,3-dihydro-1H-inden-1-ylamine were initially charged in 170 ml of methoxybenzene under a nitrogen atmosphere and cooled to 5° C. 7.61 g (75.1 mmol) of conc. (36%) HCl were then metered in and the mixture was stirred for 30 minutes. At 80 mbar and with heating to 90-115° C., a mixture of water and methoxybenzene was distilled off until water stopped passing over. The remaining suspension was then admixed with 0.52 g (1.84 mmol) of the amino-N{N-[(1R,2S)-2,6-dimethyl-2,3-dihydro-1H-inden-1-yl]carbamimidoyl}iminomethanaminium chloride to be produced (obtained from a preliminary experiment) and heated to 145° C. 6.88 g (81.0 mmol) of cyanoguanidine were then added over two hours at 145-147° C. The mixture was stirred at about 147° C. for a further 4 hours and then cooled. At 90° C. initially 0.5 g of PEG 2000 and 41.1 g (295 mmol) of dry, pulverized potassium carbonate were added. At 95° C. initially 9.0 g, and after one hour a further 2.0 g, (103 mmol in total) of (R)-methyl 2-fluoropropionate were metered in. The reaction mixture was stirred at 95° C. for a total of 5 hours.

This was followed by cooling to 50° C., filtering and warm washing twice with 10 ml of methoxybenzene in each case. The filtrates were concentrated on a rotary evaporator.

The residue was taken up in 40 ml of methanol and the product was gradually precipitated by addition of water. The solid was suctioned off, washed twice with water and dried to a constant weight in a vacuum drying cabinet.

This afforded 20.5 g of N-[(1R,2S)-2,6-dimethyl-2,3-dihydro-1H-inden-1yl]-6-[(1R)-1-fluoroethyl]-1,3,5-triazine-2,4-diamine.

EXAMPLE 6 (AS PER INVENTION ASPECT B)

Under conditions analogous to those mentioned in example 5, benzylamine afforded the corresponding triazine in 58% yield.

EXAMPLE 7 (AS PER INVENTION ASPECT B)

Under conditions analogous to those mentioned in example 5, cis-4-phenyl-cyclohexylamine afforded the corresponding triazine in 51% yield.

The invention claimed is:

1. A process for producing one or more biguanidine salts of formula (III), wherein a) an amine of formula (I) is converted into a salt (II) with an acid $H^+A^-$, b) cyanoguanidine and 0.5 to 10 mol percent of the biguanidine salt (III) to be produced, based on the amine of formula (I), in a polar aprotic solvent are metered in with stirring at elevated temperature, c) after cooling the thus obtained reaction mixture is suctioned off, washed with solvent and dried, and d) where the substituents are as defined hereinbelow:

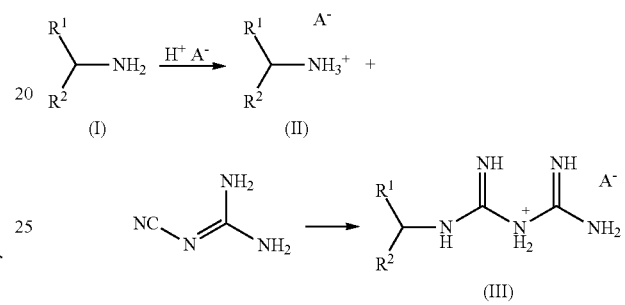

$R^1$ is hydrogen, $(C_1-C_8)$-alkyl, $(C_3-C_8)$-cycloalkyl, phenyl, naphthyl, or $(C_1-C_4)$-alkylphenyl, wherein the four last-mentioned radicals are substituted by n radicals selected from the group consisting of methyl, ethyl, propyl and methoxy, $R^2$ is $(C_1-C_8)$-alkyl, $(C_3-C_8)$-cycloalkyl, phenyl, naphthyl, or phenyl-$(C_1-C_4)$-alkyl, wherein these four abovementioned radicals are substituted by n radicals selected from the group consisting of methyl, ethyl, propyl, methoxy and $(C_3-C_4)$-cycloalkyl, or $R^1$ and $R^2$ together with the carbon atom to which they are bonded form a radical selected from the group consisting of $(C_3-C_8)$-cycloalkyl, phenyl-$(C_3-C_8)$-cycloalkyl,

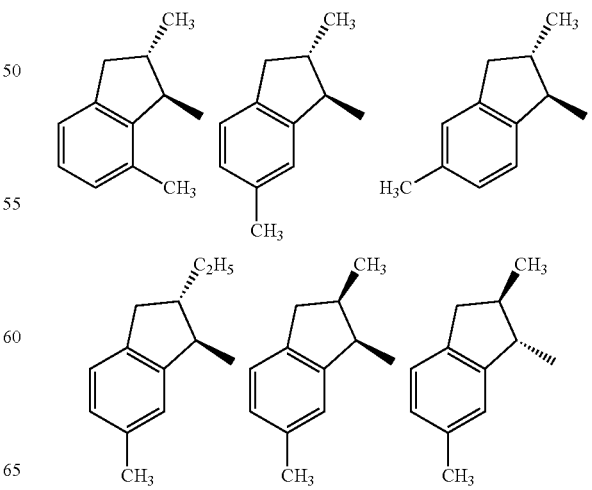

-continued

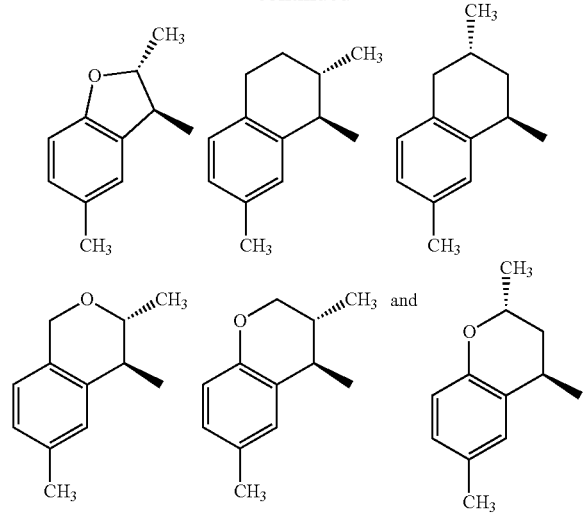

A⁻ is an anion of an acid,
n is 0, 1, 2 or 3.

2. The process as claimed in claim 1, wherein
R¹ is hydrogen, $(C_1-C_8)$-alkyl, $(C_3-C_8)$-cycloalkyl, phenyl, or $(C_1-C_4)$-alkylphenyl, wherein the three last-mentioned radicals are substituted by n radicals selected from the group consisting of methyl, ethyl, propyl and methoxy,
R² is $(C_1-C_8)$-alkyl, $(C_3-C_8)$-cycloalkyl, phenyl, naphthyl or phenyl-$(C_1-C_4)$-alkyl,
or
R¹ and R² together with the carbon atom to which they are bonded form a radical selected from the group consisting of $(C_3-C_8)$-cycloalkyl, phenyl-$(C_3-C_8)$-cycloalkyl,

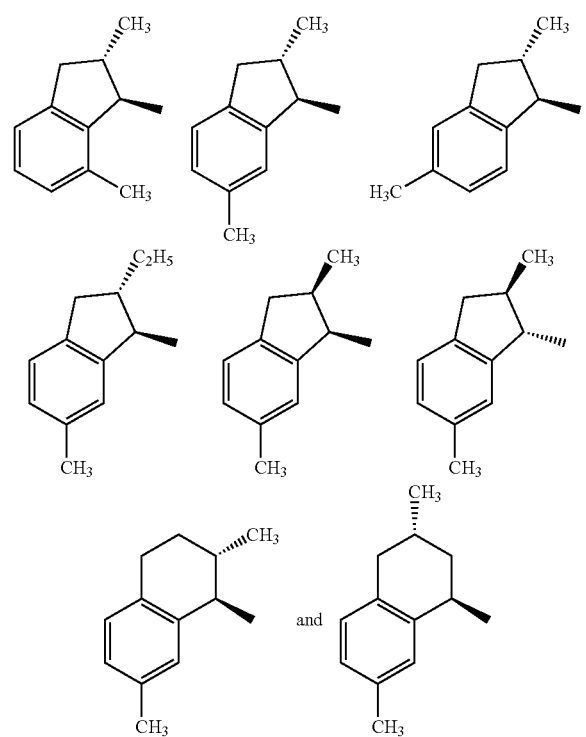

A⁻ is Cl⁻, Br⁻ or $HSO_4^-$,
n is 0, 1, 2 or 3.

3. The process as claimed in claim 1, wherein
R¹ and R² together with the carbon atom to which they are bonded form the radical

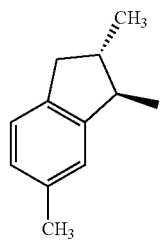

and
A⁻ is Cr.

4. A process for producing one or more s-triazines of formula (V), wherein
a) an amine of formula (I) is converted into a salt (II) with an acid H⁺A⁻,
b) cyanoguanidine and 0.5 to 10 mol percent of the biguanidine salt (III) to be produced, based on the amine of formula (I), in a polar aprotic solvent are metered in with stirring at elevated temperature,
c) after complete reaction a phase transfer catalyst and a base are added,
d) a carboxylic acid derivative of formula (IV) is metered in, and
e) where the substituents are as defined hereinbelow:

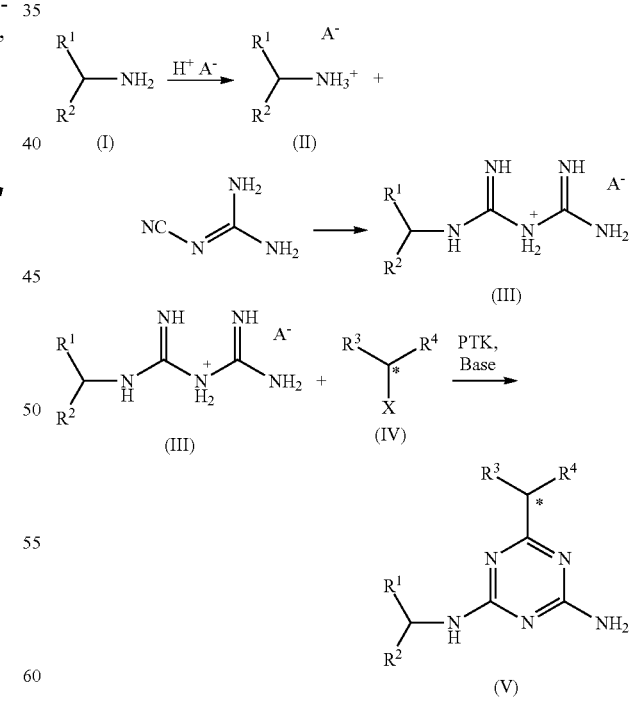

R¹ is hydrogen, $(C_1-C_8)$-alkyl, $(C_3-C_8)$-cycloalkyl, phenyl, naphthyl, or $(C_1-C_4)$-alkylphenyl, wherein the four last-mentioned radicals are substituted by n radicals selected from the group consisting of methyl, ethyl, propyl and methoxy, R² is hydrogen, (C₁-C₈)-alkyl, (C₃-C₈)-cycloalkyl, phenyl, naphthyl, or phenyl-(C₁-C₄)-alkyl, wherein these four abovementioned radicals are substituted by n radicals selected from the group consisting of methyl, ethyl, propyl, methoxy and (C₃-C₄)-cycloalkyl,
or
R¹ and R² together with the carbon atom to which they are bonded form a radical selected from the group consisting of (C₃-C₈)-cycloalkyl, phenyl-(C₃-C₈)-cycloalkyl,

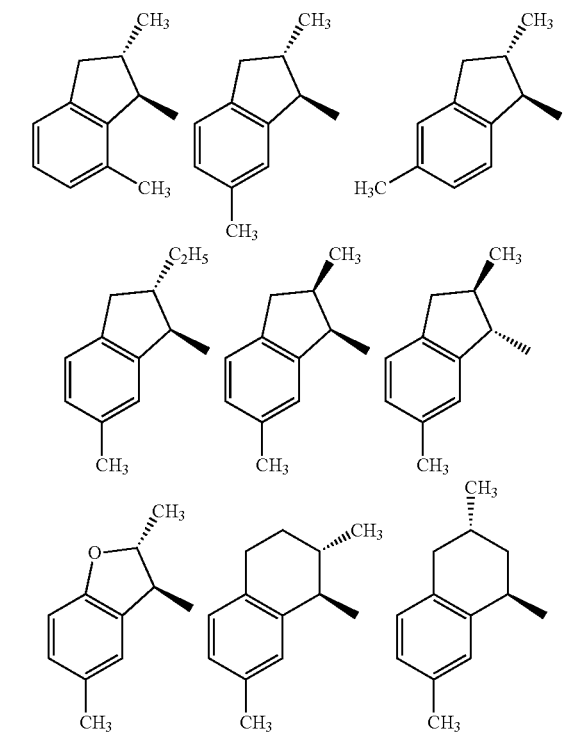

A⁻ is an anion of an acid,
n is 0, 1, 2 or 3,
R³ is hydrogen, halogen, (C₁-C₆)-alkyl, (C₁-C₆)-alkoxy, (C₃-C₈)-cycloalkyl, or phenyl, wherein the three last-mentioned radicals are substituted by n radicals selected from the group consisting of methyl, ethyl, propyl and methoxy,
R⁴ is hydrogen, halogen, (C₁-C₆)-alkyl, (C₁-C₆)-alkoxy, (C₃-C₈)-cycloalkyl, or phenyl, wherein the three last-mentioned radicals are substituted by n radicals selected from the group consisting of methyl, ethyl, propyl and methoxy,
X is (C₁-C₆)-alkoxycarbonyl, cyano or chlorocarbonyl.

5. The process as claimed in claim 4, wherein
R¹ is hydrogen, (C₁-C₈)-alkyl, (C₃-C₈)-cycloalkyl, phenyl, or (C₁-C₄)-alkylphenyl, wherein the three last-mentioned radicals are substituted by n radicals selected from the group consisting of methyl, ethyl, propyl and methoxy, R² is (C₁-C₈)-alkyl, (C₃-C₈)-cycloalkyl, phenyl, or phenyl-(C₁-C₄)-alkyl,
or
R¹ and R² together with the carbon atom to which they are bonded form a radical selected from the group consisting of (C₃-C₈)-cycloalkyl, phenyl-(C₃-C₈)-cycloalkyl,

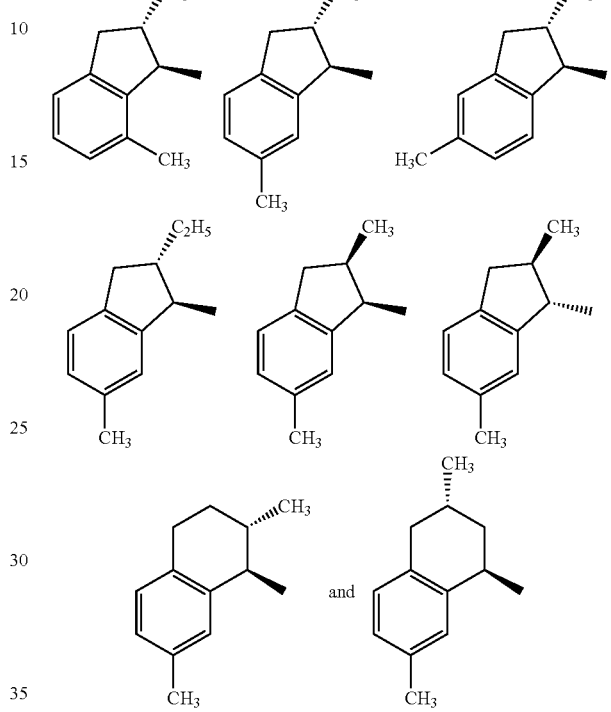

A⁻ is Cl⁻, Br⁻ or HSO₄⁻,
n is 0, 1, 2 or 3,
R³ is hydrogen, chlorine, fluorine, (C₁-C₆)-alkyl or (C₁-C₆)-alkoxy,
R⁴ is hydrogen, chlorine, fluorine, (C₁-C₆)-alkyl or (C₁-C₆)-alkoxy,
X is (C₁-C₆)-alkoxycarbonyl.

6. The process as claimed in claim 4, wherein
R¹ and R² together with the carbon atom to which they are bonded form the radical

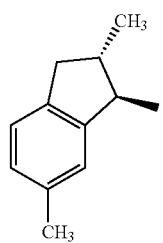

A⁻ is Cl⁻,
R³ is fluorine,
R⁴ is methyl,
X is (C₁-C₆)-alkoxycarbonyl.

7. The process as claimed in claim 1, wherein the reaction in b) is carried out at a temperature from 100° C. to the boiling point of the solvent and with an excess of 5% to 10% of cyanoguanidine based on the amine salt of formula (II).

8. The process as claimed in claim 7, wherein the reaction in b) is carried out in anisole.

9. The process as claimed in claim 1, wherein the reaction in b) is carried out with 0.5 to 2 mol percent of the biguanidine salt (III) to be produced.

10. The process as claimed in claim 4, wherein the reaction in c) is carried out with 0.5 to 5 mol percent, based on the amine of formula (I), of a polyethylene glycol as the phase-transfer catalyst.

11. The process as claimed in claim 4, wherein the reaction in c) is carried out with 100-400 mol percent, based on the amine of formula (I), of a base from the group consisting of potassium carbonate, sodium carbonate, lithium carbonate, calcium carbonate and magnesium carbonate.

12. The process as claimed in claim 11, wherein the reaction is carried out with 100-150 mol percent of potassium carbonate based on the amine of formula (I).

13. The process according to claim 1, wherein a) through d) are carried out under a protective gas atmosphere.

14. The process according to claim 13, wherein the gas is argon.

* * * * *